United States Patent [19]

Morfin

[11] Patent Number: 5,763,433
[45] Date of Patent: Jun. 9, 1998

[54] PHARMACEUTICAL COMPOSITIONS CONTAINING 3-BETA-HYDROXYLATED 6,7-SUBSTITUTED STEROID DERIVATIVES, AND USE THEREOF

[75] Inventor: Robert Morfin, Paris, France

[73] Assignee: Conservatoire National des Arts et Metiers, Paris, France

[21] Appl. No.: 416,868

[22] PCT Filed: Oct. 19, 1993

[86] PCT No.: PCT/FR93/01029

§ 371 Date: Jun. 21, 1995

§ 102(e) Date: Jun. 21, 1995

[87] PCT Pub. No.: WO94/08588

PCT Pub. Date: Apr. 28, 1994

[30] Foreign Application Priority Data

Oct. 20, 1992 [FR] France ............................ 92 12548

[51] Int. Cl.[6] .................................................. A61K 31/56
[52] U.S. Cl. ............................................ 514/177; 514/178
[58] Field of Search ............................ 514/171, 177, 514/178

[56] References Cited

U.S. PATENT DOCUMENTS

| | | | |
|---|---|---|---|
| 4,628,052 | 12/1986 | Peat | 514/171 |
| 4,898,694 | 2/1990 | Schwartz et al. | 514/171 |
| 5,077,284 | 12/1991 | Loria et al. | 260/397.5 |

FOREIGN PATENT DOCUMENTS

| | | |
|---|---|---|
| 3812595 | 10/1988 | Germany . |
| WO 91/04030 | 4/1991 | WIPO . |
| WO 92/03925 | 3/1992 | WIPO . |

*Primary Examiner*—Theodore J. Criares
*Attorney, Agent, or Firm*—Nixon & Vanderhye P.C.

[57] ABSTRACT

A pharmaceutical composition containing 7-hydroxylated derivatives of natural steroid hormones having, if necessary, a 3β hydroxyl function, for use as an immunity trigger or stimulant (hereinafter termed "immunity effector"), particularly for cell immunity. Said pharmaceutical compositions may also be used as anti-glucocorticoid agents.

26 Claims, 1 Drawing Sheet

Fig. 1

PHARMACEUTICAL COMPOSITIONS CONTAINING 3-BETA-HYDROXYLATED 6,7-SUBSTITUTED STEROID DERIVATIVES, AND USE THEREOF

This application is a 371 of PCT/FR93/01029 filed 19 Oct. 1993.

The present invention relates to pharmaceutical compositions containing as active ingredient 7-hydroxylated derivatives of natural steroid hormones optionally possessing a 3-beta hydroxyl function, and their use as a trigger or stimulator of immunity (designated hereafter as "immunity effector"), more particularly of cellular immunity; these pharmaceutical composition may also be used as anti-glucocorticoid agents.

The family of 3-beta-hydroxylated steroid hormones comprises: pregnenolone known as 3-beta-hydroxy-5-pregnen-20-one (designated hereafter by PREG), dehydroepiandrosterone known as 3-beta-hydroxy-5-androsten-17-one (designated hereafter by DHEA), androstenediol known as 5-androstene-3-beta, 17-beta-diol (designated hereafter by 5-DIOL), iosandrosterone or epiandrosterone known as 3-beta-hydroxy-5-alpha-androstan-17-one (designated hereafter by ISOA) and androstanediol known as 5-alpha-androstane-3-beta, 17-beta-diol (designated hereafter by ADIOL).

PREG is known to be the precursor of all of the steroid hormones. PREG is formed irreversibly from cholesterol in tissues and organs like the cortical part of the adrenal glands, the gonads (E. Baulieu, Hormones, Publ. Hermann (1978) and brain (Z. Hu et al., Proc. Nat. Acad. Sci. USA, 84, 8215–8219 (1987)). Formed at a very early age, the circulating quantities of it are high and relatively stable (E. DePeretti and E. Mappus, J. Clin. Endocr. Metab. 57, 550–556, (1983)). It can be converted into progesterone even in the brain (Y. Akwa et al., J. Cell. Biol., 121, 135–143 (1993)) but its irreversible conversion into mineralocorticoid and glucocorticoid hormones only occurs in the adrenocortical glands (E. Baulieu, Hormones, Publ. Hermann (1978)).

DHEA is a 17-ketosteroid which is quantitatively one of the major adrenocortical steroid hormones present in the blood of humans and other mammals. M. E. Windholz, the Merck Index, Ninth Edition (1976); K. Diem and C. Lentner, Geigy Scientific Tables (1975); E. Barret-Connor et al., N.E.J.M. 315, 1519–1524 (1986). Although DHEA seems to serve as intermediate in the synthesis of the steroids of the gonads, its primary physiological function is not clear. It is known however that the plasma concentrations of this hormone, which are maximal in the second decade of life, then decline, ultimately to reach 5% of the original level in elderly people.

In certain cases DHEA exhibits properties of an immunity effector: in R. M. Loria, T. H. Inge, S. S. Cook, A. Z. Szakl and W. Regelson (1988), J. Med. Virol., 26, 301–314, it enables the survival of mice infected by the human viruses Edwards CVB4 or HSV2 to be increased when it is injected by the subcutaneous route in amounts of the order of 1 g/kg 4 hours prior to viral infection. This effect is also observed when DHEA is administered by the oral route (0.4% in the diet) for 16 weeks before infection.

More generally, the same authors in the U.S. Pat. No. 5,077,284 demonstrate a positive effect on patients suffering from AIDS treated with doses of 400 to 2500 mg/day, and recommend the use of DHEA together with an antiviral at doses of 25 mg/kg to 2 g/kg.

The irreversible production of DHEA from PREG is known to occur particularly in adrenocortical tissue and in the gonads (E. Baulieu, Hormones, Publ. Hermann (1978)). Moreover, DHEA is only produced from the time of adrenarche and the circulating amount of it increases with puberty (E. DePeretti and E. Mappus, J. Clin. Endocr. Metab., 57, 550–556 (1983)). Once mature, considerable quantities of DHEA circulate in the blood of adult human and other mammals but these quantities reach a maximum in the second decade of human life then decline to ultimately attain less than 10% of the original level in very old people (N. Orentreich et al., J. Clin. Endocr. Metab., 59, 551–555 (1984)).

5-DIOL is derived directly from DHEA, the 17-ketone function of which is reduced by an oxidoreductase. Its circulating quantities are low compared with those of DHEA since the oxidoreduction also acts in the opposite sense to give DHEA and androgens like testosterone may be derived from it even in the skin (I. Faredin and I. Toth, Acta Med. Acad. Sci. Hung., 32, 139–152 (1975)).

In the gonads DHEA and 5-DIOL are successively converted irreversibly into androgenic hormones (testosterone), then estrogens (estradiol) by a series of known enzymatic reactions (E. Baulieu, Hormones, Publ. Hermann (1978)).

Testosterone is reduced irreversibly in the target tissues to its androgenically active derivative, 5-alpha-dihydrotestosterone. It is from this steroid that ADIOL and ISOA are derived by reversible enzymatic reactions (E. Baulieu, Hormones, Publ. Hermann (1978)). The circulating amounts of these two steroids are low in the adult and are zero before puberty and almost zero after menopause and andropause (P. Mauvais-Jarvis and G. Charransol, Nvelle Presse Médic, 23, 1565–1569 (1973); C. Hopkinson et al., J. Steroid Biochem., 8, 1253–1257 (1977); G. Habrioux et al., Steroids, 32, 61–71 (1978)).

The use of PREG has never been considered for therapeutic purposes since this steroid is the precursor of all of the steroid hormones. On the other hand, DHEA has effects which have been demonstrated in different pathological conditions, including in particular cancer, diabetes, ageing, obesity. These different effects are described in a series of articles collected in a recent monograph on the biochemical, biological and clinical effects of DHEA (The biologic role of dehydroepiandrosterone, editors: M. Kalimi and W. Regelson, Publication: Walter de Gruyter, Berlin, N.Y., 1990). The precise mode of action of DHEA is studied there but still not explained with certainty. All of the publications indicate that to obtain an effect, DHEA must be administered either orally or subcutaneously in high doses ranging from 25 mg/kg to 2g/kg in repeated administrations.

However, the use of DHEA in a therapeutic or prophylactic composition is confronted with three problems.
- the low solubility of DHEA in aqueous solutions
- the need to inject it several hours before the antigen to obtain the desired effect,
- the considerable quantities necessary for the production of an effect may well lead to prohibitive costs and undesirable side effects.

Similarly, 5-DIOL has recently been used to obtain an enhanced antiviral response in the mouse. The selected efficacious doses range from 20 mg/kg to 320 mg/kg after subcutaneous administration or 0.4% by weight of the diet (R. Loria and D. Padgett, Arch. Virol., 127, 103–115 (1992) ). The known side effects of 5-DIOL nonetheless considerably limit its therapeutic use in man.

Finally, ADIOL and ISOA are not used or contemplated as therapeutic agents owing to their relatively strong androgenic action (P. Robel et al., Biochemie, 53, 81–96 (1971)).

3-beta-hydroxylated steroids like PREG, DHEA, 5-DIOL are hydroxylated at position 7 in many tissues as has already been shown in the rat (Y. Akwa et al., Biochem. J. 288, 959–964 (1992)) and the mouse (R. Morfin and G. Courchay, J. Steroid Biochem. Molec. Biol., (in press)). In the case of ADIOL and ISOA hydroxylations at position 6 or 7 have been demonstrated in man (R. Morfin et al., Biochimie, 59, 637–644 (1977)), in the rat (J. Guiraud, R. Morfin et al., Steroids, 34, 241–248 (1979)) and in the dog (R. Morfin et al., Eur. J. Biochem., 109, 119–127 (1980)). This discovery has been confirmed and extended in man (F. Jacolot et al., J. Steroid Biochem., 14, 663–669 (1981); S. Tunn et al., J. Steroid Biochem., 28, 257–263 (1987)) and in the rat (J. Isaacs et al., Steroids, 33, 639–657 (1979); M. Warner et al., Endocrinology, 124, 2669–2706 (1979)). These hydroxylations at positions 6 or 7 are specific for the 3-beta-hydroxylated steroids and the enzymatic process is irreversible.

Hence it emerges that the 6 or 7-hydroxylated steroids formed cannot give rise to classical steroid hormones such as the mineralocorticoids, glucocorticoids, progestins, androgens and estrogens and they appear to be inactive in the areas in which these latter hormones are active (A. Sunde et al., J. Steroid Biochem., 16, 483–488 (1982); F. Celotti et al., J. Steroid Biochem., 18, 197–401 (1983)).

Various recent articles also demonstrate the existence of an association between the endocrine and immune systems; in this connection it has been suggested that DHEA might play an anti-glucocorticoid regulatory role (A. Meikle et al., J. Steroid Biochem. Molec. Biol., 42, 293–304 (1992)), although studies with this steroid have given only negative results (P. Mohan and M. Cleary, Steroids, 57, 244–247 (1992)).

The objective of the present invention is to attempt to solve the different problems raised above concerning the therapeutic use of DHEA or PREG and results from the discovery according to which not only the microsomes of rat brain but the skin, the intestine, the colon, the caecum, the spleen, the thymus and the brain of the mouse are capable of converting DHEA and pregnenolone into polar derivatives, more water-soluble than the 7-alpha-hydroxylated derivatives. 7-beta-hydroxylated derivatives have also been detected. Furthermore, the quantity of 7-alpha-hydroxylated derivatives increases with the age of the animals.

The present invention relates to pharmaceutical compositions containing as active ingredient compounds of the general formula (I):

or the general formula (II):

in which the substituents R, $R_1$ and $R_2$ have the following meanings:

R=—H or ester function of 1 to 100 carbon atoms,
in which the substituents R, $R_1$ and $R_2$ have the following meanings:
R=—H or ester function of 1 to 100 carbon atoms,
$R_1$=—$H_2$ or =O (ketone)
    or beta-OH (hydroxyl)
    or beta-CO-$R_3$
    or beta-CHOH-$R_3$
    with $R_3$ being an alkyl group comprising from 1 to 4 carbon atoms, and preferably methyl,
$R_2$=—H or halogen,
the substituents at 6, 7 and 16 may be in the alpha or beta position, in combination with a pharmaceutical vehicle.

In the preferred compounds of the invention, R is hydrogen, $R_1$ is a =O or a —CO—$CH_3$ function.

In the compounds of formula I or II the hydrogens at positions 6 and 7 may be replaced by a ketone.

In addition, in the general formula II, the radicals at 6 and 7 may be mutually exclusive or be present in the same molecule.

The invention relates more particularly to the pharmaceutical compositions in which the compounds of the type in question are combined with a pharmaceutical vehicle appropriate to the mode of administration selected.

The pharmaceutical compositions of the invention containing as active ingredient a compound of formula I or formula II may be used as cellular immunity effectors, in particular in:
  the prevention of the development of AIDS by treatment of the subjects seropositive for HIV1, HIV2 and other retroviruses responsible for this syndrome,
  the prevention and treatment of neoplastic processes such as cancers of the skin, intestine, mammary glands, nervous system, adrenal glands, gonads and leukemias,
  the prevention and treatment of the auto-immune diseases such as systemic lupus erythematosus,
  the treatment of the dysfunctioning of the hypothalamo-hypophyseal-adrenal axis,
  the prevention of immunosuppression due to stress, and of the decline of natural immunity with age or any other type of immunosuppression.

The invention also relates to the use of the molecules of formula I or II in the manufacture of a pharmaceutical composition which can be used as anti-glucocorticoid in all of the therapeutic uses implicating the search for an action to counter that of the natural or synthetic glucocorticoids.

The diseases concerned are all those in which the use of glucocorticoid agents is medically inadvisable as well as those resulting from the undesirable side effects of these same glucocorticoids.

Included in these diseases associated with glucocorticoids and with undesirable side effects due to glucocorticoids may be mentioned as examples:

Cushing's syndrome, adrenal tumours, disorders of the hypothalamo-hypophyseal-adrenal axis, the diabetogenic and immunosuppressor effects of the glucocorticoids, weakness, muscular atrophy, delays in cicatrisation and thinning of the skin due to glucocorticoids, digestive ulcers, osteoporosis, mobilization of fatty acids and accumulation of the fats resulting from taking glucocorticoids, cataracts in the adult and the diminution of growth of children treated with glucocorticoids, opportunistic infections, dysmenorrhea, insomnias and depressive states resulting from excessive treatments with or actions of glucocorticoids.

The maximal pharmacological effect of these compounds is obtained by any route of administration conveying the active molecule to the target cells, including in particular oral, subcutaneous, percutaneous, intramuscular or topical administration.

An advantageous dosage of the compounds of formula I or II used in the production of the therapeutic composition ranges from 1 to 100 mg/kg in mammals.

For the purposes of administration of a steroid organic solvents are usually used in the human and animal pharmacopoeia. Particular use is made of:

DMSO (dimethyl sulfoxide) for intramuscular or subcutaneous injection;

the solvents for steroids injectable by the subcutaneous or intramuscular route which are usually plant oils (ricin, olive, peanut, . . . ) sometimes hydrogenated or neutralized. Some steroids are also injected in the form of a suspension in carboxymethyl cellulose;

the transcutaneous administrations (ointments, gels) using in particular mixtures (formulary and excipients) which include alcohols (ethylene, propylene glycols), fatty alcohols (stearyl, octyl-2-dodecanol, $C_{20}$ . . . ), vaseline, plants oils (ricin, olive . . . ).

Novel formulations also allow delayed transepithelial or transcutaneous absorption. They consist of inclusions in polyvinylpyrrolidone or in polyethylene glycol or in matrices polymerized with smoked silica.

Administration to the codon may make use of the rectal route with suppositories (cocoa butter) but also the oral route with cyclodextrins which trap the hydrophobic active principle and, on being destroyed, release it into the colon (J. Szetli, Pharmaceut. Technol. Int., 3, 16–24 (1991)).

Finally, the invention relates to the medicines which can be used as immunity effectors or are designed for the prevention or treatment of diseases or symptoms resulting from the action of glucocorticoids characterized in that they contain a compound of formula I or formula II in combination with a pharmaceutical vehicle appropriate to the mode of administration selected.

The different examples which follow show in a nonlimiting manner the therapeutic effects of the 7-alpha- or 7-beta-hydroxylated derivatives both as immunity effectors and as anti-glucocorticoid agents.

I—IMMUNITY EFFECTOR EFFECT

The immunity effector effect was tested by subcutaneous injection concomitantly with that of an antigen and the 7-alpha- or 7-beta-hydroxylated derivative into C57BL/6 mice according to a standard immunization protocol (Methods in Enzymology (1980), vol. 70).

The effect of the compound as cellular immunity effector is measured by the quantity of circulating IgG directed against the antigen 21 days after the injection and after a booster injection 14 days layer.

The following, non-limiting examples described the invention:

EXAMPLE I

Effect of 7-alpha-OH-DHEA and 7-beta-OH-DHEA
Preparation (Synthesis) of 7-alpha- and 7-beta-hydroxydehydroepiandrosterone DHEA acetate (1) (1 g, Sigma D-45000), is converted into 3-beta-acetoxy, 7-alpha-bromoandrost-5-en-17-one (2) by the procedure published by J. ORR and J. BROUGHTON (J. Org. Chem. (1970) 35, 1126–1129) using N-bromosuccinimide under light irradiation.

The brominated derivative obtained is converted into a mixture of 3-beta, 7-alpha (beta)- diacetoxy-androst-5-en-17-one (3) by treatment with the mixture of K acetate/acetic acid according to A. NUSSBAUM et al. (J. Am. Chem. Soc. (1960) 82, 2641).

The mixture obtained is saponified in refluxing methanolic $K_2CO_3$ for 3 hours. After extraction of the saponified steroids, 3-beta, 7-alpha-dihydroxy-androst-5-en-17-one (4) is separated from 3-beta, 7-beta-dihydroxy-androst-5-en-17-one (5) by preparative chromatography on silica gel with ethyl acetate as eluent. The 7-beta epimer is eluted first, completely separated from the 7-alpha steroid which is then eluted.

(4) is crystallized from ethyl acetate/n-hexane. The crystals (120 mg) melt at 182°–183° C., in agreement with the finding of R. DODSON et al. (J. Am. Chem. Soc. (1959) 81, 6295–6297) and G. DEFAYE et al. (J. Steroid Biochem. (1978) 9, 331–336).

(5) is crystallized in the same manner (280 mg). The crystals melt at 214°–215° C., in agreement with the finding of the same authors mentioned above.

Analysis of (4) and (5) by gas chromatography coupled to mass spectrometry in the form of di-trimethylsilyloxy derivatives gives for each a molecular ion at 448 corresponding to the expected mass and the same retention times and fragmentation profiles as those for the same reference derivatives (4) and (5) (supplied by H. A. LARDY, University of Wisconsin).

Immunization Protocol

Thirty five groups of five 6-weeks old C57BL/6 mice are given a subcutaneous injection of 200 ug of hen egg white lysozyme on days one and fourteen of the immunization protocol. Solutions of DHEA (Sigma D-4500) in dimethyl sulfoxide (DMSO) are injected in the same manner at variable times before the first injection of lysozyme. Amounts ranging from 0.25 and 2 g/kg are used. Ten other groups of 5 mice are given a subcutaneous injection of 6.25 to 50 mg/kg of 7-alpha-hydroxy-DHEA or 7-beta-hydroxy-DHEA dissolved in DMSO at the same time as the first lysozyme injection. Two groups receive only DMSO with lysozyme (controls). The blanks correspond to one group of 5 mice and are not given an injection.

Three weeks after the first injections the animals, then aged 9 weeks, are decapitated. The blood of each animal is collected and the presence of anti-lysozyme G immunoglobulins (IgG) is measured in serial dilutions of the sera by an immunoenzymatic titration using goat anti-mouse (Fc) IgG immunoglobulin labelled with peroxidase.

The results are indicated in lines 1, 3, 6 and 7 of Table 1, where the particularly marked effect of the low doses of 7-alpha-OH-DHEA is apparent. 7-beta-OH-DHEA has an effect equivalent to that of DHEA injected 1 hour before the antigen, but at doses 20 times lower.

EXAMPLE II

Effect of 7-alpha-OH and 7-beta-OH Pregnenolone
Preparation (Synthesis) of 7-alpha- and 7-beta-hydroxy-pregnenolone Pregnenolone acetate (1) (Sigma, P-9254) is converted into 3-beta-acetoxy-7-alpha-bromopregn-5-en-20-one (2) by the procedure published by J. ORR and J. BROUGHTON (J. Org. Chem. (1970) 35. 1126–1129) using N-bromosuccinimide under light irradiation.

The brominated derivative obtained is converted into a mixture of 3-beta, 7-alpha (beta)- diacetoxy-androst-5-en-17-one (3) by treatment with the mixture of K acetate/acetic acid according to A. NUSSBAUM et al. (J. Am. Chem. Soc. (1960) 82, 2641).

The mixture obtained is saponified in refluxing methanolic $K_2CO_3$ for 3 hours. After extraction of the saponified steroids, 3-beta, 7-alpha-dihydroxy-androst-5-en-17-one (4) is separated from 3-beta, 7-beta-dihydroxy-androst-5-en-17-one (5) by preparative chromatography on silica gel with ethyl acetate as eluent. The 7-beta epimer is eluted first, completely separated from the 7-alpha steroid which is then eluted.

(4) is crystallized from ethyl acetate/n-hexane. The crystals are checked by nuclear magnetic resonance (200 MHz), 0.55 (3H, s, Me-18), 0.99 (3H, s, Me-19), 2.13 (3H, s, Me-21), 3.62 (1H, m, H-3), 3.86 (1H, s, H-7), 5.62 (1H, d, H-6). The analysis of the di-trimethylsilyloxy derivative of (4) in gas chromatography coupled to mass spectrometry gives the expected molecular ion at 476 and the corresponding fragmentation profile.

(5) is crystallized from ethyl acetate/n-hexane. The crystals are checked by nuclear magnetic resonance (200 MHz), 0.63 (3H, s, Me-18), 1.05 (3H, s, Me-19), 2.12 (3H, s, Me-21), 3.53 (1H, m, H-3), 3.83 (1H, d, H-7), 5.30 (1H, s, H-6). The analysis of the di-trimethylsilyloxy derivative of (4) in gas chromatography coupled to mass spectrometry gives the expected molecular ion at 476 and the corresponding fragmentation profile.

Immunization Protocol

This is carried out in the same manner as that described in Example I.

The results are indicated on lines 2 and 5 of Table 1.

EXAMPLE III

Effect of Androst-5-ene-3-beta, 7-alpha (beta), 17-beta) Triol (7-alpha-OH ADIOL and 7-beta-OH ADIOL)

Preparation (Synthesis) of Androst-5-ene-3-beta, 7-alpha (beta), 17-beta) Triol (7-alpha-OH ADIOL and 7-beta-OH ADIOL)

Dehydroepiandrosterone acetate (DHEA) (1) (Sigma, D-4500) is oxidized at position 7 by means of the $CrO_3$-dimethylpyrazole complex according to SALMOND et al. (J. Org. Chem. (1978) 43, 2057) and leads to 3-beta-acetoxyandrost-5-ene-17-dione (2). This product is identical (melting point, chromatographic Rf, UV absorption, mass spectrum) with that supplied as reference material by J. JACQUES (Collège de France).

(2) is reduced by NaBH4 in methanol to lead to the mixture of 3-beta-acetoxy-7-alpha (beta), 17-beta-dihydroxy-androst-5-ene epimers (3). After saponification of the mixture (3) in KOH/methanol, androst-5-ene-3-beta, 7-alpha, 17-beta-triol (4) and androst-5-ene-3-beta, 7-beta, 17-beta-triol (5) are obtained successively, completely separated by means of chromatography on silica gel with ethyl acetate as eluent.

(4) and (5) are crystallizee from acetone/n-hexane. The crystals of (4) melt at 272°–273° C. in agreement with the findings of G. DEFAYE et al. (J. Steroid Biochem. (1978) 9, 331–336) and its tri-trimethylsilyloxy derivative shows the expected molecular ion at 522 and the corresponding fragmentation profile after gas phase chromatography coupled with mass spectrometry.

The crystals of (5) melt at 244°–245° C. in agreement with the finding of G. DEFAYE et al. (J. Steroid Biochem. (1978) 9, 331–336) and its tri-trimethylsilyloxy derivative shows the expected molecular ion at 522 and the corresponding fragmentation profile after gas phase chromatography coupled with mass spectrometry.

Immunization

A group of 5 mice is given the subcutaneous injection of 125 mg/kg of 5-androstene-3-beta, 17-beta-diol (ADIOL) one hour prior to the first injection of lysozyme, and two groups of 5 mice are treated with 25 mg/kg of 7-alpha-hydroxy-ADIOL or 7-beta-hydroxy-ADIOL at the time of the first lysozyme injection.

Results

The results are indicated on lines 4, 8 and 9 of Table 1 below.

Table 1: Immunoenzymatic measurements of the anti-lysozyme IgG present in the serum of C57BL/6 mice immunized against lysozyme after treatment with pregnenolone (PREG) or DHEA or androst-5-ene-3-beta, 17-beta-diol or their 7-hydroxylated derivatives or in the absence of steroid.

DHEA or PREG or ADIOL is injected subcutaneously 1 hour before the first lysozyme injection. The 7-hydroxylated derivatives are administered simultaneously with the lysozyme injection. The immunoenzymatic measurement of the anti-lysozyme IgGs in the serial dilutions of the sera of each animal makes use of goat anti-mouse (Fc) IgG immunoglobulin, labelled with peroxidase in 96-well plates treated with lysozyme. The mean value of the optical densities measured in each group of 5 mice is calculated as well as the standard deviation (SD).

TABLE 1

Calculated from measurements on higher dilutions of the serum.

| Steroid injected | Optical densities +/− SD in the serial dilutions | | |
|---|---|---|---|
| | 1/180 | 1/540 | |
| 1. Controls (zero) | 0,15 ± 0,01 | 0,13 ± 0,01 | 0,10 ± 0,01 |
| 2. PREG (0,5 g/kg) | *4,67 ± 1,21 | 1,83 ± 0,48 | 0,56 ± 0,15 |
| 3. DHEA (1,0 g/kg) | 0,40 ± 0,06 | 0,26 ± 0,04 | 0,14 ± 0,02 |
| 4. ADIOL (125 mg/kg) | 0,26 ± 0,09 | 0,37 ± 0,06 | 0,22 ± 0,03 |
| 5. 7-hydroxy-PREG (6,25 mg/kg) | *4,46 ± 0,30 | *2,20 ± 0,14 | 0,77 ± 0,05 |
| 6. 7-hydroxy-DHEA (6,25 mg/kg) | 1,21 ± 0,37 | 0,74 ± 0,21 | 0,43 ± 0,12 |
| 7. 7β-hydroxy-DHEA (50,0 mg/kg) | 0,46 ± 0,06 | 0,31 ± 0,04 | 0,13 ± 0,01 |
| 8. 7-hydroxy-ADIOL (25,0 mg/kg) | 0,15 ± 0,02 | 0,14 ± 0,01 | 0,11 ± 0,01 |
| 9. 7β-hydroxy-ADIOL (25,0 mg/kg) | 0,18 ± 0,06 | 0,18 ± 0,02 | 0,12 ± 0,01 |

PREG, DHEA and ADIOL increase the serum concentrations of anti-lysozyme IgG when these steroids are administered at least one hour prior to the injection of lysozyme. The best responses are obtained with 0.5 g/kg of PREG and 1 g/kg of DHEA (Table 1). When these steroids are injected simultaneously with lysozyme, the amounts of IgG are identical with those found in the controls.

On the other hand, the 7-alpha-hydroxylated derivatives of PREG and DHEA trigger an enhanced production of IgG when they are administered simultaneously with lysozyme. The smallest quantity injected (6.25 mg/kg) is the most active (Table 1). The injection under these conditions of 50 mg/kg of 7-beta-hydroxy-DHEA gives a response identical with that of 1 g/kg of DHEA administered 1 hour prior to that of lysozyme (Table 1). At the dose tested, the 7-hydroxylated derivatives of ADIOL lead to only a very slight increase in the serum anti-lysozyme IgGs (Table 1).

These results relate the tissue hydroxylation of the natural precursors of the steroid hormones to the triggering of the immune response. The latency time for the action of PREG or DHEA to lead to an increase in the anti-lysozyme IgG involves the conversion of these steroids into active metabolites. The demonstration of their hydroxylation at 7-alpha in cutaneous tissues and the demonstration of the immediate effect of these 7-alpha-hydroxylated derivatives on the enhanced production of anti-lysozyme IgG provide proof of this. The study of the hydroxylations of 3-beta-hydroxylated steroids in various tissues in several species (R. Morfin, S. DiStefano, J. F. Charles and H. H. Floch (1977) Biochimie, 59, 637–644; J. T. Isaacs, I. R. McDermott and D. S. Coffey (1979), Steroids, 33, 675–692; M. Warmer, P. Tollet, M. Strömstedt, K. Carlström and J. A. Gustafsson (1989), J. Endocrinol., 122, 341–349; Y. Akwa, R. Morfin, P. Robel and E. E. Baulieu (1992), Biochem. J., 288, 959–964; R. Morfin, unpublished results on mice) has proved that hydroxylation at 7 is predominantly 7-alpha but with small amounts of 7-beta. It is also apparent that the 7-alpha-hydroxy-DHEA is much more active than its 7-beta epimer. Nonetheless, the fact remains that the 7-beta epimers and the compositions containing them must also be considered as forming part of the invention.

These examples are give as illustrations but are not limiting neither with respect to the dose used nor by the presence of a 5–6 double bond in the steroid, nor by the effect observed on the synthesis of the IgG 7-alpha-hydroxylated DHEA constitutes a natural metabolite of DHEA which might explain the difficulties observed previously with DHEA. In fact, the quantities of DHEA necessary for the demonstration of the physiological effects observed by various authors (The biologic role of dehydroepiandrosterone, editors M. Kalimi, W. Regelson, publication Walter de Gruyter, Berlin, N.Y., 1990) and the fact that a stimulatory effect on immunity required an injection prior to that of the antigen are perhaps with hindsight explained by the fact that the activities observed for DHEA are necessarily mediated by prior metabolism of this steroid.

II—ANTI-GLUCOCORTICOID EFFECT

The anti-glucocorticoid effect of these molecules has been proved by the studies of their competition with radio-labelled dexamethazone bound to the nucleus in the cells of hepatic, cerebral, spleen and thymic tissues in the C57BL/6 mouse according to the protocol published by P. Mohan and M. Cleary on rat hepatocytes (Steroids, 57, 244–247 (1992)). This experimental protocol is itself an adaptation of the method of D. Colvar et al. (Clin. Chem., 34, 363–369 (1988)).

The following, non-limiting examples describe the invention.

Figure 1:
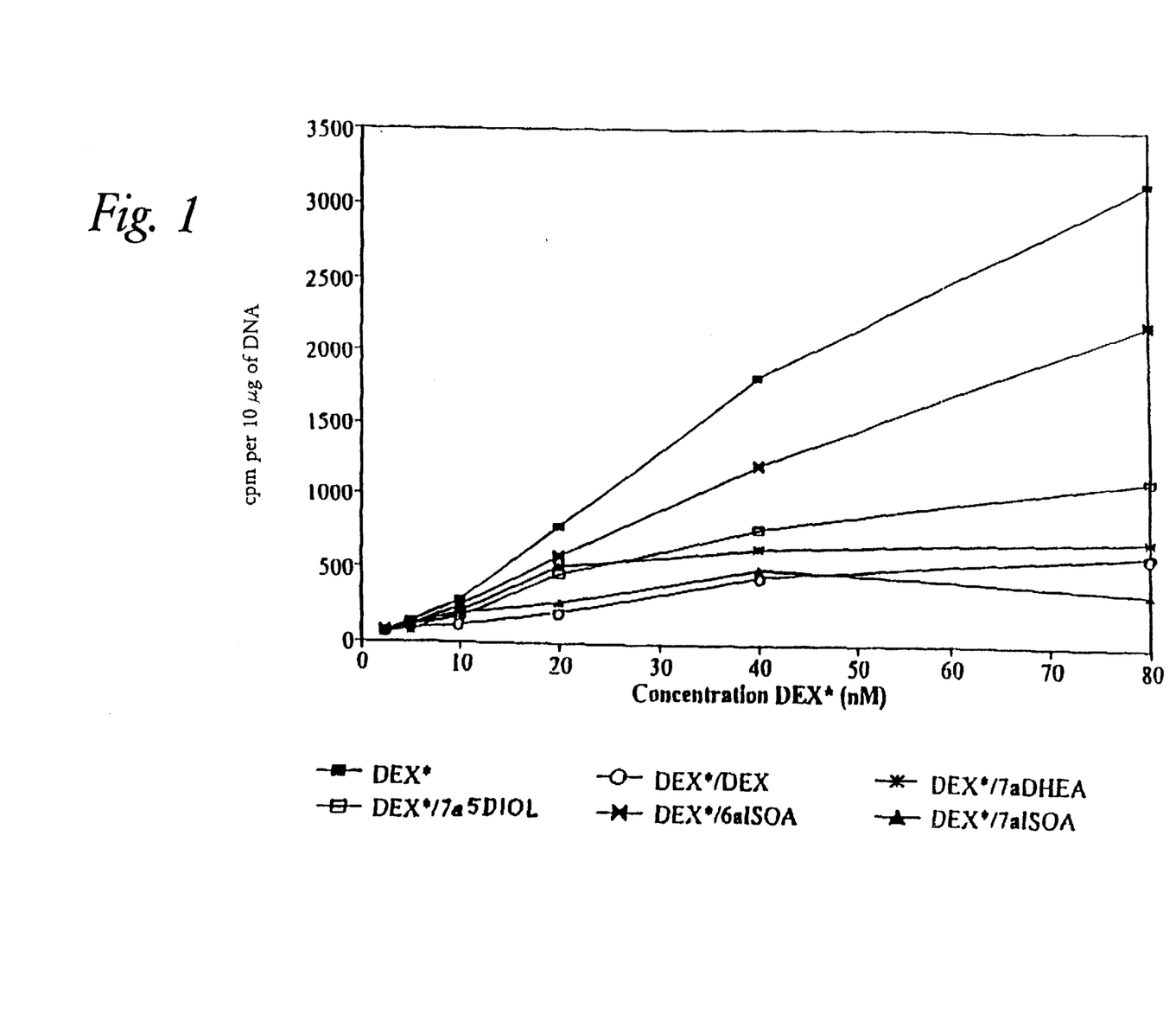
FIG. 1 illustrates the displacement of the nuclear binding of tritiated dexamethazone as described herein.

FIG. 1 shows the anti-glucocorticoid effect of different derivatives tested, measured by competition with radioactive dexamethazone for binding to rat hepatocyte nuclei.

The isolated hepatocytes are incubated for 1 hour at room temperature with increasing concentrations (2–80 nM) of $^3$H-dexamethazone (DEX*). The same incubations are repeated in the presence of a 100-fold excess (200–8000 nM) of unlabelled dexamethazone (DEX*/DEX) or 7-alpha-hydroxy DHEA (DEX*/7-alpha-DHEA) or 7-alpha-hydroxy-5DIOL (DEX*/7-alpha-5DIOL) or 6-alpha-hydroxy-ISOA). The hepatocyte nuclei are then isolated and purified and the radioactivity corresponding to the DEX* still bound is measured and expressed in cpm/10 ug of DNA. The area under the curve DEX* corresponds to zero displacement of the radioactivity. The area under the curve DEX*/DEX which corresponds to the displacement of radioactivity by the same molecule is taken arbitrarily as 100. The areas under the curve obtained with the other steroids makes it possible to calculate by interpolation between the areas zero and 100 their displacement coefficients for the nuclear binding of DEX*.

The fact that the steroids tested which are shown to be the most active are natural derivatives of the androgenic steroid hormones assumes its full significance on consideration of the many interactions observed during treatments with combinations of glucocorticoids and anabolizing androgenic steroids (O. Linet, Progr. Drug Res., 14, 139–195 (1970)). The "anti-glucocorticoid" effects observed following these treatments are very variable and can now be explained by the need for prior metabolism of the androgenic steroids administered so that the active 7-hydroxylated derivatives are produced.

This observation thus suggests that the synthetic steroid molecules recognized as possessing an effect similar to that of their natural parent such as 16-bromo-ISOA (A. Schwartz et al., Adv. Cancer Res., Publ. Academic Press, 51, 391–424 (1988); G. Gordon et al., Adv. Enzyme Regul., Publ. Pergamon Press, 26, 355–382 (1987)) be given consideration. The possible conversion of such a steroid into a particularly active 6- or 7-oxygenated derivative leads us thus to consider that these derivatives and the compositions containing them form part of the invention.

The precise mechanism of the interaction of the 6- or 7-oxygenated steroids with the DNA-glucocorticoid receptor complex has not been resolved; nonetheless, the anti-glucocorticoid effect observed in each of the examples given may be considered as a non-limiting illustration of the derivatives which can be used to the extent that they comply with one of the formulae I or II above. These examples are also not limiting with respect to the dose or the route of administration used or therapeutic effects resulting from their use.

EXAMPLE IV

Anti-glucocorticoid Effect of 7-alpha-hydroxy-DHEA and 7-beta-hydroxy-DHEA

Preparation (Synthesis) of 7-alpha- and 7-beta-hydroxy-DHEA

This is carried out as in Example I.

Test of Anti-glucocorticoid Activity

Seven to twelve weeks old C57BL/6 mice are treated with metyrapone (25 mg/kg) 24 hours and 12 hours before being sacrificed so as to diminish their level of natural glucocorticoids and to increase the cellular concentrations of specific glucocorticoid receptors (R. Rupprecht et al., J. Neuroendocr., 2, 803–806 (1990)). The mice are anesthetized with ether and bled, then perfused intracardially with physiological serum containing collagenase B (0.03 g/100 ml) for 10 minutes. The liver, brain, spleen and thymus are excised and the cells of each organ are recovered by the method described (P. Mohan and M. Cleary, Steroids, 57, 244–247 (1992)). The quantities of cells obtained are estimated on the base of the measurement of the DNA contained in the preparations. The cells are incubated for 1 hour at room temperature in the presence of increasing quantities (2 nM to 80 nM) of tritiated dexamethazone supplemented or not with a 100 times greater quantity of unlabelled dexamethazone or one of the compounds to be tested.

The nuclei are recovered and their radioactive content measured as described by the authors cited above.

The corresponding results are plotted (FIG. 1) such that the radioactivity measured per 10 ug of cellular DNA is expressed as a function of the molarity of tritiated dexamethazone in the incubation mixture. The expected displacement of tritiated dexamethazone by unlabelled dexamethazone is observed. The area under the curve of tritiated dexamethazone alone is measured and taken as zero. The area under the curve of tritiated dexamethazone supplemented with a 100 fold excess of unlabelled dexamethazone is measured and taken as 100. The areas under the curve for each of the unlabelled steroids tested by the individual addition of a quantity 100 fold greater than tritiated dexamethazone are measured and their displacement coefficients for tritiated dexamethazone bound to the nuclei are calculated by interpolation between zero and 100.

The results obtained for each of the four organs with 7-alpha-hydroxy-DHEA and 7-beta-hydroxy-DHEA are shown on lines 1 and 2 of Table 2. The displacement of tritiated dexamethazone which they cause in the nuclei demonstrate their anti-glucocorticoid action, 7-alpha-hydroxy-DHEA being more effective that the 7-beta epimer.

EXAMPLE V

Anti-glucocorticoid Effect of 7-alpha-hydroxy-PREG and 7-beta-hydroxy-PREG

Preparation (Synthesis) of 7-alpha- and 7-beta-hydroxy-PREG

The preparation is identical with that described in Example II.

Test of Anti-glucocorticoid Activity

This is carried out in the same manner as in Example IV.

The results are indicated on lines 3 and 4 of Table 2. The displacement of tritiated dexamethazone which they cause in the nuclei demonstrates their anti-glucocorticoid effect.

EXAMPLE VI

Effect of 5-androstene-3-beta, 7-alpha (beta), 17-beta-triols (7-alpha-hydroxy-5DIOL and 7-beta-hydroxy-5DIOL)

Preparation (Synthesis) of 7-alpha-hydroxy-5DIOL and 7-beta-hydroxy-5DIOL

The preparation is identical with that described in Example III.

Test of Anti-glucocorticoid Activity

This is carried out in the same manner as in Example IV.

Only 7-alpha-hydroxy-5DIOL is tested on hepatocyte nuclei. The results are shown on line 5 of Table 2. The displacement of tritiated dexamethazone bound in hepatocyte nuclei by 7-alpha-hydroxy-5DIOL demonstrates its anti-glucocorticoid effect.

EXAMPLE VII

Effect of the 6- and 7-oxygenated Derivatives of 3-beta-hydroxylated and 5-alpha-reduced Steroids Preparation (Synthesis) of 3-beta-hydroxy-5-alpha-androstane-7,17-dione (7-oxo-ISOA), 3-beta, 6-alpha-dihydroxy-5-alpha-androstane-17-one (6-alpha-hydroxy-ISOA), 3-beta, 7-alpha-dihydroxy-5-alpha-androstane-17-one (7-alpha-hydroxy-ISOA), 3-beta, 7-beta-dihydroxy-5-alpha-androstane-17-one (7-beta-hydroxy-ISOA), 5-alpha-androstane-3-beta, 7-alpha, 17-beta-triol (7-alpha-hydroxy-ADIOL) and 5-alpha-androstane-3-beta, 7-beta, 17-beta-triol (7-beta-hydroxy-ADIOL)

We have carried out the synthesis and identification and measured the chromatographic properties of these steroids and published them in detail (A. Kerebel, R. Morfin, F. Berthou et al., J. Chromatogr., 140, 229–244 (1977)).

Two other steroids are commercially available: 3-beta-hydroxy-5-pregnen-7,20-dione (7-oxo-PREG) Steraloids Inc., Q5400) and 3-beta-hydroxy-5-androsten-7,17-dione (7-oxo-DHEA) (Steraloids Inc., A8320).

Tests of Anti-glucocorticoid Activity

These were carried out with these molecules in the same manner as in Example I. The results obtained are shown on lines 6, 7, 8, 9, 10, 11 and 12 of Table 2 where the derivatives of ISOA and ADIOL are all shown to be very active.

Legend to Table 2

The following steroids designated 1 to 13 are: 1. 7-alpha-hydroxy-DHEA (7-alpha-OH-DHEA), 2. 7-beta-hydroxy-DHEA (7-beta-OH-DHEA), 3. 7-alpha-hydroxy-PREG (7-alpha-OH-PREG), 4. 7-beta-hydroxy-PREG (7-beta-hydroxy-PREG), 5. 7-alpha-hydroxy-5DIOL (7-alpha-OH-5DIOL), 6. 7-alpha-hydroxy-ISOA (7-alpha-OH-ISOA), 7. 7-beta-hydroxy-ISOA (7-beta-OH-ISOA), 8. 7-alpha-hydroxy-ADIOL (7-alpha-OH-ADIOL), 9. 6-alpha-hydroxy-ISOA (6-alpha-OH-ADIOL), 10. 7-oxo-PREG, 11. 7-oxo-DHEA, 12. 7-oxo-ISOA, 13. dexamethazone (DEX).

The displacement of the nuclear binding of tritiated dexamethazone by a 100-fold greater concentration of each of these steroids is measured as shown in FIG. 1. The absence of steroid competitor is taken as zero, and the presence of unlabelled dexamethazone is taken as 100. The displacement coefficients found for each of the other steroids are calculated by interpolation on this scale, each result being the mean of a triplicate determination.

TABLE 2

| Steroid tested | Liver | Brain | Thymus | Spleen |
|---|---|---|---|---|
| 1. 7α-OH-DHEA | 95 | 49 | 85 | 91 |
| 2. 7β-OH-DHEA | 80 | 65 | — | — |
| 3. 7α-OH-PREG | 34 | 38 | 94 | 81 |
| 4. 7β-OH-PREG | 82 | — | — | — |
| 5. 7α-OH-5DIOL | 88 | — | — | — |
| 6. 7α-OH-ISOA | 102 | — | — | — |
| 7. 7β-OH-ISOA | 68 | — | — | — |
| 8. 7α-OH-ADIOL | 83 | 96 | 96 | 125 |
| 9. 6α-OH-ISOA | 63 | — | — | — |
| 10 7-oxo-PREG | 35 | — | — | — |
| 11 7-oxo-DHEA | 28 | — | — | — |
| 12 7-oxo-ISOA | 84 | — | — | — |
| 13 DEX | 100 | 100 | 100 | 100 |

The results presented above show that the 7-hydroxylated derivatives of DHEA, ISOA and 5-DIOL actively displace tritiated dexamethazone from its nuclear binding. The displacements with other steroids are significant but less marked. The fact that these results are expressed with respect to the displacement obtained by equivalent quantities of unlabelled dexamethazone, and out earlier observation (French patent application No. 92.12548) demonstrating an immunoactivating effect of these same steroids in the mouse which implies the blocking of the known immunosuppressor effect of the glucocorticoids suggests the use of the steroids tested in a pharmaceutical composition for an anti-glucocorticoid treatment.

Dexamethazone is a synthetic steroid which undergoes only slight metabolism (H. Siebe et al., Renal Physiol. Biochem., 16, 79–88 (1993)) and which possesses an affinity for the cytosolic receptor of the glucocorticoids higher than that of the natural glucocorticoids such as corticosterone or cortisol. The fact that the binding of the cytosolic receptor-dexamethazone complex to nuclear recognition sites is diminished by the steroids tested confirms the potentiality of an anti-glucocorticoid effect. Furthermore, our studies (not reported here) show that cytosolic or nuclear receptors specific for 7-alpha-hydroxy-DHEA do not exist but its effect leading to the activation of immune processes may be considered as essentially anti-glucocorticoid.

I claim:

1. Pharmaceutical composition containing a compound of general formula I (I)

or of general formula II:

(II)

in which:

R=—H or ester function of 1 to 100 carbon atoms, $R_1$=—$H_2$ or =O (ketone)
  or beta-OH (hydroxyl)
  or beta-CO-$R_3$
  or beta-CHOH-$R_3$
  with $R_3$ being an alkyl group comprising from 1 to 4 carbon atoms, and preferably methyl, substituted or unsubstituted, $R_2$=—H or halogen, or a carbonitrile radical, the substituents at 6, 7 and 16 may be in the alpha or beta position, and, optionally, the hydrogens at position 6 or 7 may be replaced by a ketone, the compounds of formula I or formula II being combined in said composition with an acceptable pharmaceutical vehicle.

2. Composition according to claim 1 characterized in that the compound and the pharmaceutical vehicle are combined in a formulation permitting oral, cutaneous, subcutaneous or topical administration.

3. A pharmaceutical composition comprising a compound of the formula:

(I)

or of formula II:

(II)

wherein:

R=—H or ester function of 1 or 100 carbon atoms, $R_1$=—$H_2$ or =O (ketone)
  or beta-OH (hydroxyl)
  or beta-CO-$R_1$
  or beta-CHOH-$R_3$ $R_3$=an alkyl group comprising from 1 to 4 carbon atoms, $R_2$=—H or halogen, or a carbonitrile radical, the substituents at 6, 7 and 16 are in the alpha or beta position, and optionally, the hydrogens at position 6 or 7 are replaced by a ketone, wherein said composition allows the administration of 1 to 100 milligrams of the compound per kg in mammals.

4. A pharmaceutical composition comprising a compound of the formula:

(I)

or of formula II;

(II)

wherein:

R=—H or ester function of 1 to 100 carbon atoms,

$R_1$=—$H_2$ or =O (ketone)
  or beta-OH (hydroxyl)
  or beta-CO-$R_3$
  or beta-CHOH-$R_3$

$R_3$=an alkyl group comprising from 1 to 4 atoms, $R_2$=—H or halogen, or a carbonitrile radical, the substituents at 6, 7 and 16 are in the alpha or beta position, and, optionally, the hydrogens at position 6 or 7 are replaced by a ketone, and an active vaccinating agent.

5. A method of preventing the development of AIDS by treatment of a seropositive subject for HIV1, HIV2 and other retroviruses responsible for AIDS comprising administering a compound of the formula:

(I)

(I)

or of formula II:

(II)

wherein:

R=—H or ester function of 1 to 100 carbon atoms,

$R_1$=—$H_2$ or =O (ketone)
  or beta-OH (hydroxyl)
  or beta-CO-$R_3$
  or beta-CHOH-$R_3$ $R_3$=an alkyl group comprising from 1 to 4 carbon atoms,

$R_2$=—H or halogen, or a carbonitrile radical, the substituents at 6, 7 and 16 are in the alpha or beta position, and, optionally, the hydrogens at position 6 or 7 are replaced by a ketone.

6. A method of preventing or treating cancer comprising administering to a mammal in need of such treatment a compound of the formula:

(I)

or of formula II:

(II)

wherein:

R=—H or ester function of 1 to 100 carbon atoms,

$R_1$=—$H_2$ or =O (ketone)
  or beta-OH (hydroxyl)
  or beta-CO-$R_3$
  or beta-CHOH-$R_3$ $R_3$=an alkyl group comprising from 1 to 4 carbon atoms,

$R_2$=—H or halogen, or a carbonitrile radical, the substituents at 6, 7 and 16 are in the alpha or beta position, and, optionally, the hydrogens at position 6 or 7 are replaced by a ketone.

7. A method of preventing or treating auto-immune disease comprising administering to a mammal in need of such treatment a compound of the formula:

(I)

or of formula II:

(II)

wherein:

R=—H or ester function of 1 to 100 carbon atoms, $R_1$=—$H_2$ or =O (ketone)
  or beta-OH (hydroxyl)
  or beta-CO-$R_3$
  or beta-CHOH-$R_3$

$R_3$=an alkyl group comprising from 1 to 4 carbon atoms, $R_2$=—H or halogen, or a carbonitrile radical, the substituents at 6, 7 and 16 are in the alpha or beta position, and, optionally, the hydrogens at position 6 or 7 are replaced by a ketone.

8. A method for treating dysfunctioning of the hypothalamo-hypophyseal-adrenal axis comprising administering to a mammal in need of such treatment a compound of the formula:

17 or of formula II:

wherein:

R=—H or ester function of 1 to 100 carbon atoms,
$R_1$=—$H_2$ or =O (ketone)
or beta-OH (hydroxyl)
or beta-CO-$R_3$
or beta-CHOH-$R_3$ $R_3$=an alkyl group comprising from 1 to 4 carbon atoms,
$R_2$=—H or halogen, or a carbonitrile radical,
the substituents at 6, 7 and 16 are in the alpha or beta position, and, optionally, the hydrogens at position 6 or 7 are replaced by a ketone.

9. A method of preventing immuno-suppression comprising administering to a mammal in need of such treatment a compound of the formula:

or of formula II:

wherein:

R=—H or ester function of 1 to 100 carbon atoms,
$R_1$=—$H_2$ or =O (ketone)
or beta-OH (hydroxyl)
or beta-CO-$R_3$
or beta-CHOH-$R_3$

$R_3$=an alkyl group comprising from 1 to 4 carbon atoms,
$R_2$=—H or halogen, or a carbonitrile radical,
the substituents at 6, 7 and 16 are in the alpha or beta position, and, optionally, the hydrogens at position 6 or 7 are replaced by a ketone.

18

10. A method of increasing the immunogenic response of a vaccinating antigen comprising administering to a mammal a vaccinating antigen and a compound according to the formula:

or of formula II:

wherein:

R=—H or ester function of 1 to 100 carbon atoms,
$R_1$=—$H_2$ or =O (ketone)
or beta-OH (hydroxyl)
or beta-CO-$R_3$
or beta-CHOH-$R_3$ $R_3$=an alkyl group comprising from 1 or 4 carbon atoms,
$R_2$=—H or halogen, or a carbonitrile radical,
the substituents at 6, 7 and 16 are in the alpha or beta position, and, optionally, the hydrogens at position 6 or 7 are replaced by a ketone.

11. A method of treating or preventing viral, bacterial, fungal or parasitic disease comprising administering to a mammal in need of such treatment a compound of the formula:

or of formula II:

wherein:

R=—H or ester function of 1 to 100 carbon atoms,
$R_1$=—$H_2$ or =O (ketone)
or beta-OH (hydroxyl)
or beta-CO-$R_3$
or beta-CHOH-$R_3$ $R_3$=an alkyl group comprising from 1 to 4 carbon atoms,
$R_2$=—H or halogen, or a carbonitrile radical,
the substituents at 6, 7 and 16 are in the alpha or beta position, and, optionally, the hydrogens at position 6 or 7 are replaced by a ketone.

12. A method of delivering an antagonist of glucocorticoids comprising administering to a mammal in need of such treatment a compound of the formula:

(I)

or of formula II:

(II)

wherein:
R=—H or ester function of 1 to 100 carbon atoms,
$R_1$=—$H_2$ or =O (ketone)
or beta-OH (hydroxyl)
or beta-CO-$R_3$
or beta-CHOH-$R_3$
$R_3$=an alkyl group comprising from 1 to 4 carbon atoms,
$R_2$=—H or halogen, or a carbonitrile radical,
the substituents at 6, 7 and 16 are in the alpha or beta position, and, optionally, the hydrogens at positions 6 or 7 are replaced by a ketone.

13. A method of treating the pathological effects of glucocorticoids comprising administering to a mammal in need of such treatment a compound of the formula:

(I)

or of formula II:

(II)

wherein:
R=—H or ester function of 1 to 100 carbon atoms,
$R_1$=—$H_2$ or =O (ketone)
or beta-OH (hydroxyl)
or beta-CO-$R_3$
or beta-CHOH-$R_3$
$R_3$=an alkyl group comprising from 1 to 4 carbon atoms,
$R_2$=—H or halogen, or a carbonitrile radical,
the substituents at 6, 7 and 16 are in the alpha or beta position, and, optionally, the hydrogens at position 6 or 7 are replaced by a ketone.

14. Pharmaceutical composition according to claim 12, characterized in that it comprises at least one compound of formula I or formula II, which can be used alone or in combination with another compound in the treatment of dysfunctioning of the hypothalamo-hypophyseal-adrenal axis.

15. Pharmaceutical composition characterized in that it comprises at least one compound of formula I or formula II, which can be used alone or in combination with another compound in the prevention and treatment of the diabetogenic and lipidogenic effects due to glucocorticoids.

16. Pharmaceutical composition characterized in that it comprises at least one compound of formula I or formula II, which can be used alone or in combination with another compound in the prevention and treatment of muscular atrophy and weakness caused by glucocorticoids.

17. Pharmaceutical composition characterized in that it comprises at least one compound of formula I or formula II, which can be used alone or in combination with another compound in the prevention and treatment of the digestive ulcers caused by the use or an excess of glucocorticoids.

18. Pharmaceutical composition characterized in that it comprises at least one compound of formula I or formula II, which can be used alone or in combination with another compound in the prevention and treatment of osteoporosis and bone fragility resulting from the action of natural or synthetic glucocorticoids.

19. Pharmaceutical composition characterized in that it comprises at least one compound of formula I or formula II, which can be used alone or in combination with another compound in the prevention and treatment of cataracts resulting from the action of natural or synthetic glucocorticoids.

20. Pharmaceutical composition characterized in that it comprises at least one compound of formula I or formula II, which can be used alone or in combination with another compound in the prevention of the diminution of the growth of children treated with glucocorticoids.

21. Pharmaceutical composition characterized in that it comprises at least one compound of formula I or formula II, which can be used alone or in combination with another compound in the prevention and treatment of the insomnias and depressive states resulting from the action of natural or synthetic glucocorticoids.

22. Pharmaceutical composition characterized in that it comprises at least one compound of formula I or formula II, which can be used alone or in combination with another compound in the treatment of dysmenorrheas resulting from the action of glucocorticoids.

23. Pharmaceutical composition characterized in that it comprises at least one compound of formula I or formula II, which can be used alone or in combination with another compound in the prevention and treatment of the opportunistic infections favoured by the action of glucocorticoids.

24. Medicine designed for the prevention or treatment of diseases or symptoms resulting from the action of glucocorticoids, characterized in that it contains a compound of formula I or formula II in combination with a pharmaceutical vehicle appropriate for the mode of administration selected.

25. A method as in claim 6 wherein said cancer is selected from the group consisting of cancer of the skin, intestine, mammary glands, nervous system, adrenal glands, gonads and leukemia.

26. A method as in claim 7 wherein said auto-immune disease is systemic lupus erythematosus.

* * * * *